United States Patent [19]

Serkes et al.

[11] Patent Number: 4,962,033
[45] Date of Patent: Oct. 9, 1990

[54] ROLLER BOTTLE METHOD OF CULTURING CELLS

[75] Inventors: Jonathan M. Serkes, Oak View; William L. Foschaar, Camarillo, both of Calif.

[73] Assignee: In Vitro Scientific Products, Ventura, Calif.

[21] Appl. No.: 364,322

[22] Filed: Jun. 12, 1989

Related U.S. Application Data

[60] Division of Ser. No. 201,429, Jun. 2, 1988, which is a continuation-in-part of Ser. No. 130,740, Dec. 9, 1987, Pat. No. 4,824,787.

[51] Int. Cl.$^5$ .............................................. C12N 5/00
[52] U.S. Cl. ...................... 435/240.243; 435/240.23; 435/284; 435/285
[58] Field of Search ..................... 435/240.23, 240.243, 435/284, 285

[56] References Cited

U.S. PATENT DOCUMENTS

| | | | |
|---|---|---|---|
| 4,094,744 | 6/1978 | Hartdegen et al. | 435/180 |
| 4,238,568 | 12/1980 | Lynn | 435/285 |
| 4,317,886 | 3/1982 | Johnson et al. | 435/285 |
| 4,451,568 | 5/1984 | Schneider et al. | 435/180 |

FOREIGN PATENT DOCUMENTS 1191951 10/1959 France .
86/04085 7/1986 World Int. Prop. O. .

*Primary Examiner*—Robert J. Warden
*Assistant Examiner*—Timothy M. McMahon
*Attorney, Agent, or Firm*—Marvin E. Jacobs

[57] ABSTRACT

A roller bottle for cell growth contains a wall formed of a plurality of corrugations, preferably symmetrical and perpendicular to the axis of the bottle, and having at least one drain channel formed by at least one and preferably two opposed flat axial, uncorrugated panels and optionally containing axial reinforcement ribs provided along the outer edge of the corrugations. The corrugations are discontinuous along the inside surface of the panels to form drainage channels. The surface area of the bottle is 110 to 500% larger than an uncorrugated bottle having the same exterior dimensions.

20 Claims, 3 Drawing Sheets

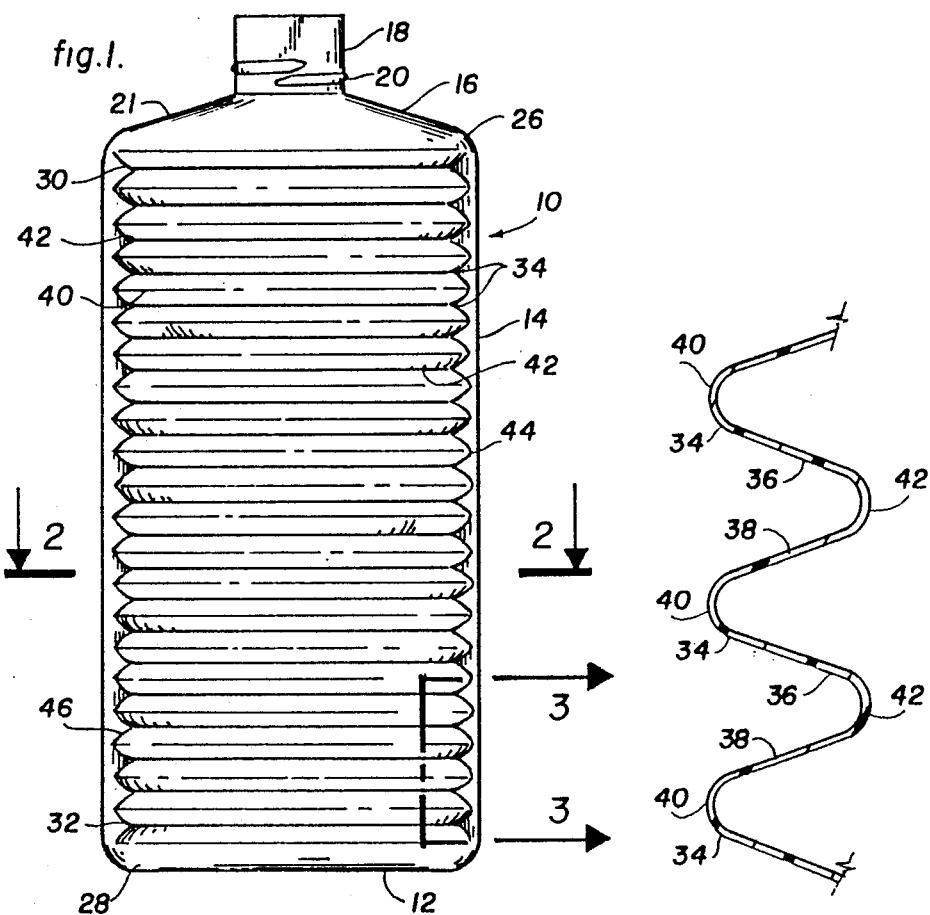
fig.1.
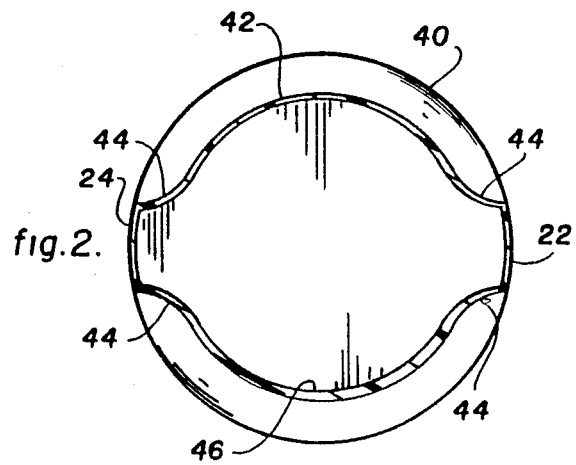
fig.2.
fig.3.

ROLLER BOTTLE METHOD OF CULTURING CELLS

CROSS-REFERENCE TO RELATED APPLICATION

This application is a division of Ser. No. 201,429 filed June 2, 1988 which is a continuation-in-part of Ser. No. 130,740 filed Dec. 9, 1987, now issued as U.S. Pat. No. 4,824,787 on Apr. 25, 1989.

DESCRIPTION

Technical Field

The invention relates to biotechnology apparatus and, more particularly, this invention relates to a roller bottle for tissue culture growth.

Genetic engineering is progressing to a commercially profitable stage with the recent government approval of several genetically engineered products—especially pharmaceutical products expressed from animal cells, such as interferon, human growth hormone, insulin, tissue plasminogen activator (TPA) and erythropoietin (EPO). It is estimated that 20% of the $60 billion of pharmaceuticals presently produced by chemical methods could be produced by simpler and more economical biotechnology methods. The next stage of the industry's growth will involve large scale cell culture.

The early protein products produced by genetic engineering were produced in single cell bacterial or yeast cells. Bacterial and viruses are simple biological cells that are not capable of producing the more complex molecules and combinations of molecules. TPA and EPO are glycoproteins. The simple proteins produced by bacteria or yeast cells must be glycosylated in a separate step. Furthermore, bacterial cells do not usually secrete the desired protein into the surrounding medium. They must be chemically or mechanically fragmented in order to harvest the desired protein.

Mammalian cells can produce sugar modified proteins and more importantly, they often secrete the desired glycoprotein product into the medium for easy collection. However, mammalian cells are very fragile. They contain a delicate membrane that is easily ruptured or damaged by abrasion from the surface of a bioreactor or by the propellers of a conventional bacterial fermenter. Once the membrane is ruptured, the cell dies.

Another difficulty with mammalian cells is that they grow slowly. Unlike bacteria which divides 2 to 3 times an hour, mammalian cells divide only every 18 to 48 hours. Also a mammalian cell is not a self-sufficient organism. It is part of a much larger organism and demands a steady stream of nutrients, hormones and other compounds to survive and grow.

Most mammalian cells must be attached to a support or substrate similar to their condition in a living organism. Many biotechnology processes culture mammalian cells while anchored to the surface of a roller bottle. In order to increase the surface area for attachment in some culture processes, the cells have been attached to inert beads, embedded in a gel or attached to the surface of a hollow fiber. These systems are complex and expensive and can result in stagnant regions which do not receive adequate nutrients and/or buildup excessive waste products.

Roller bottles have been used extensively to culture animal cells while attached to the inside surface of the bottles. There is a large number of roller bottle reactor systems in place within biotechnology and animal vaccine companies. These reactor systems are still suitable for short-term batch runs. However, the economy and efficiency could be greatly increased if the amount of cells processed per bottle could be increased.

| List of Prior Art | |
|---|---|
| PATENT NO. | PATENTEE |
| 3,249,504 | L. R. Cappel et al. |
| 3,589,983 | Holderith et al. |
| 3,893,887 | Smith et al. |
| 4,176,756 | Gellman |
| 4,238,568 | Robert W. Lynn |
| 4,283,495 | Robert W. Lynn |
| 4,317,886 | Johnson et al. |
| 4,337,104 | Robert W. Lynn |
| D 285,725 | Larry A. Franchere |
| 4,657,867 | Guhl et al. |

DESCRIPTION OF THE PRIOR ART

Johnson et al. discloses providing an extended growth surface by means of a plurality of concentric rings in the form of cylindrical inserts parallel to the axis of the bottle. Clips are required to maintain separation between the cylindrical inserts. The embodiment of FIG. 5 indicates the inserts can have a corrugated surface. The corrugations would be parallel to the axis of the bottle. The Johnson et al. bottle is manufactured in several separate parts which are then assembled and adhered together to form a sealed enclosure. The bottle is too expensive and has not provided the intended benefits. This bottle is not commercially available.

The Lynn patents require exterior circumferential serrations. Gellman relates to a stopper lock for a culture bottle. The Franchere patent relates to a rectangular tissue container. Holderith discloses a tray insert for a bottle. Smith et al discloses a method for programmed control of a tilting apparatus for roller bottles. Cappel deals with a two container system, one for the stable liquid ingredients and one for the dried, labile ingredients. Guhl et al. discloses a multicell tissue culture apparatus.

Due to the constraints of the roller apparatus, the roller bottles must have a specified circumference and length. Therefore, it was accepted that the external configuration could not be changed. Johnson added the cylindrical inserts to the roller bottle since he believed that was the only way to the increase cell attachment surface of the bottle.

STATEMENT OF THE INVENTION

An improved roller bottle with greatly increased surface area for tissue growth is provided in accordance with the invention. The roller bottle is more easily manufactured in a single step process as a unitary piece and is able to increase surface area for cell attachment without changing the external dimensions or essential configuration of the bottle.

The roller bottle of the invention contains cell growth attachment surfaces that are attached to and extend inwardly a distance from the inside surface of the bottle. In a first configuration, a plurality of baffles were attached to the wall of the bottle. These baffles significantly increased surface area of the bottle. However, it was found that some of the cells detached from the baffles during roller operation. It was found that the cells would more reliably maintain attachment to a surface that slanted, suitably by an angle of from 10° to 80° with the wall surface.

A preferred configuration for the slanted surface is provided by means of accordion-like pleats which form the side wall of the bottle. The two slanted surfaces connect to form an inner corrugation. Adjacent corrugations intersect to form a plurality of outer bands which ride on the rollers. The corrugations are preferably parallel to each other. The corrugations can be perpendicular to the axis of the bottle or can be formed at an angle to the axis such as spiral-shaped triangular pleats encircling the outside surface of the bottle. Bottles with spiral bands will tend to move along the rollers when rolled.

The bottles are periodically drained to remove waste product, harvest expressed product or to harvest cells. The corrugated, pleated surfaces act as channels for the liquid nutrient during rolling of the bottle. However, during drainage they act as dams preventing easy drainage. Another feature of the roller bottle of the invention is the provision of at least 1, preferably at least 2, drain channels in the form of an unpleated segment of the sidewall, parallel to the axis of the bottle running as a band from near the top to near the bottom of the bottle. The drain channel is formed along the outer edges of the pleats along the outer circumference of the bands so that the bottle rolls smoothly on the roller cylinders of the roller apparatus. Another benefit of the drain channels is the support they provide to the bottle. The corrugated pleats tend to be weak and can cause accordion-like stretching or compression of the bottle when handled or bending of the bottle under the weight of the liquid nutrient medium. Repeated flexing of the pleats can cause fatigue and rupture, especially during the long periods of use during the cell culturing batch process. However, the drain channels act as beams preventing bending, extension or compression of the corrugated pleats. Additional reinforcement can be provided by forming additional drain channels and/or narrower axial beams in the side wall of the bottle. The beams need not run the whole length of the bottle. They can be selectively placed in regions requiring additional strengthening such as near the bottom of the bottle. Another feature of the invention is the superior properties of plasma treated linear polyester as tissue culture substrates.

These and many other features and attendant advantages of the invention will become apparent as the invention becomes better understood by reference to the following detailed description when considered in conjunction with the accompanying drawings.

DESCRIPTION OF THE DRAWINGS

FIG. 1 is a front view in elevation of an embodiment of the roller bottle of the invention;

FIG. 2 is an enlarged, detailed view in section taken along line 2—2 of FIG. 1;

FIG. 3 is a cross-sectional view taken along line 3—3 of FIG. 1;

DETAILED DESCRIPTION OF THE INVENTION

Figure 4:
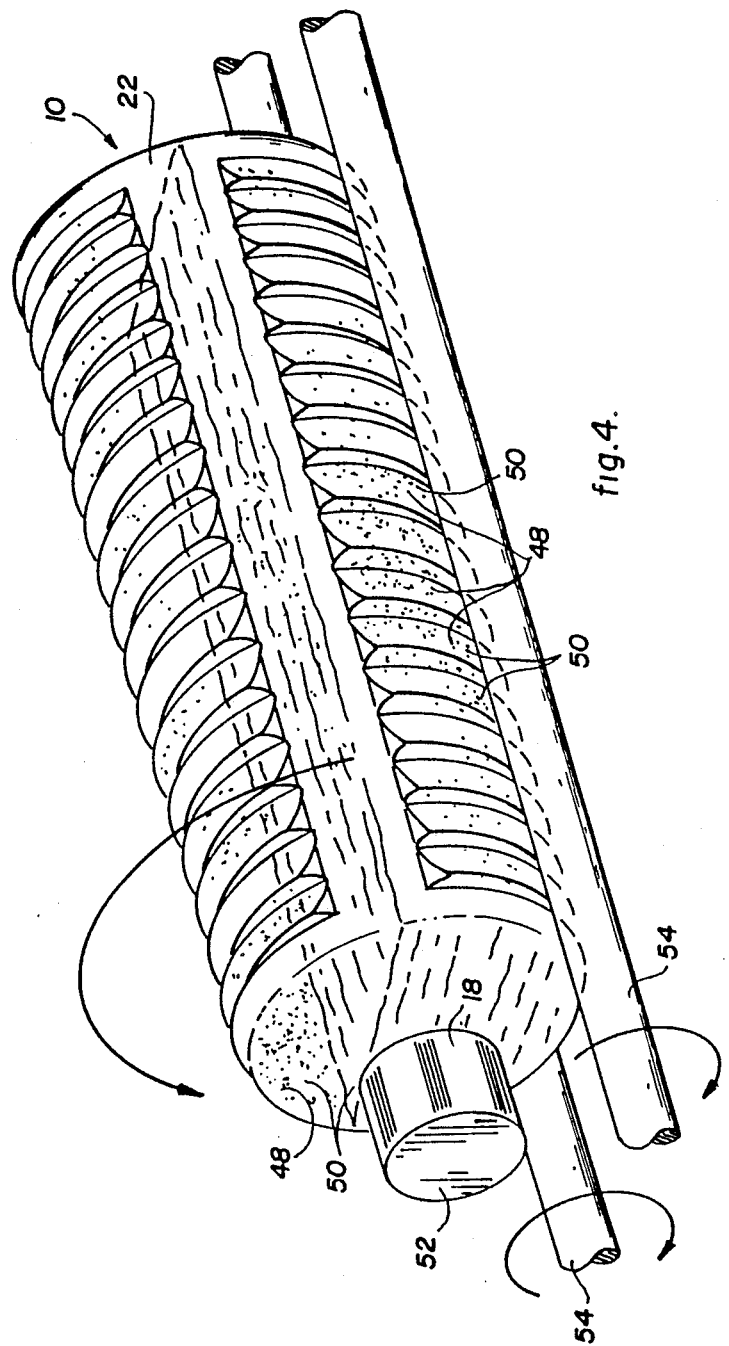
FIG. 4 is a perspective view of the roller bottle shown on a set of schematic rollers.

Referring now to FIGS. 1–3, a first embodiment of a the roller bottle 10 is illustrate as a generally cylindrical member formed of a bottom 12, a corrugated, pleated midsection 14 and a top section 16 having a neck 18 containing a spiral thread 20 for attachment of a cap, not shown. The pleated mid-section 14 contains at least one drain channel 22, preferably at least two drain channels 22, 24 disposed in opposed relation. The juncture 26 of the top and juncture 28 of the bottom with the mid-section are preferably rounded to reduce stress and fracture surfaces. Though expanses of solid wall could be provided between the bottom 12 or top 16 and the top pleat 30 or the bottom pleat 32, these wall sections are usually avoided in order to maximize the number of pleats and thus maximize the surface area.

Though some surface area of the wall is removed by the drainage channel, the surface area is increased by at least 110% over an unpleated bottle of the same exterior dimensions. The typical standard bottle is a disposable plastic bottle having a 850 cm2 surface area. The maximum surface area increase will usually be no more than 500% to maintain volume for the cell culture medium and to maintain structural integrity of the bottle. The optimum design appears to be about 175 to 250% increase in surface area. The number of pleats or corrugations depends on the amplitude of the corrugations, the pitch of the corrugations and the height and volume of the bottle. Generally, a conventional 2¼ liter roller bottle will contain 10 to 50 corrugations, usually about 20 to 40 corrugations. The widths of the panels forming the drain channels and reinforcement beams are not critical except that the panels represent a loss of increased surface area. The area of channels and support beams is are preferably maintained between 5 to 40% of the circumference of the bottle.

Referring now to FIG. 3, the pitch or angle of the corrugations 34 is designed so that the liquid culture medium drains toward the drain channels 22, 24. The corrugations in a commercial mineral water bottle are pitched downwardly so that the mineral water pours readily out of the top. The corrugations 34 in the roller bottle of the invention are preferably symmetrical with the upper surface 36 and the lower surface 38 having an equal length and pitch with respect to a plane normal to the axis of the bottle through the inner juncture 40 of the two surfaces 36, 38. The juncture 40 is preferably rounded since it is easier for the cells to stick to a rounded rather than a sharp, pointed surface and the rounded juncture is easier to form by casting or molding. A rounded surface is also stronger and less subject to cracking on flexing.

The radius of the curved edge of the juncture 40 is at least 0.010 inches preferably from 0.05 to 0.10 inches. The amplitude can be from 0.2 to 0.5 inches, generally about 0.3 to 0.4 inches. This provides a spacing of about 0.1 to 0.5 inches between corrugations 34.

The bottle is manufactured from a biocompatible, resin material that can be subject to radiation for sterilization and surface treatment which provides a wettable surface for attachment of the cells. Surface treatment can be a coating, corona discharge or plasma. The resin material should also be able to withstand longterm rolling in the environment of the roller apparatus. The roller bottle of the invention can be manufactured in a single stage by various molding procedures.

The wall of the bottle has a sufficient thickness to form a bottle of adequate strength when filled with cell culturing medium. Generally, the film thickness will be from 1 to 60 thousands for a 2.25 liter roller bottle. The resin must be able to readily flow to form the small radius corrugations. The resin must not have any extractibles in order to be approved by the FDA for use in biotechnology processes. Earlier attempt to utilize plasma treated polystyrene bottles resulted in areas where cells did not attach, possibly due to the presence of plasticizer or other polymerization additive on the surface. More uniform and faster cell attachment is achieved using linear polyester resins for forming the bottles which is plasma treated. Transparent, thermoplastic resins such as polyethyleneglycol-polyesters or copolyesters such as PET or PETG Copolyester 6763 (copolymer of ethylene glycol and 1, 4 cyclohexanedimethanol), have been found suitable for forming the roller bottle of the invention by extrusion blow or injection blow molding techniques. The copolyester can be used to form bottles by extrusion blow molding.

Referring again to FIGS. 1 and 2, the outer circumferential surface for rolling the bottle 10 is formed by the two panels 22, 24 of the drains and the rims 42 forming the outer junctures of the walls 36, 38 of the corrugations 34. The inner terminus of each corrugation 34 adjacent the drain channels 24, 26 is faced with a triangular wall 44 which slopes toward the channel 22, 24 acting as a smooth ramp for channelling the liquid or suspension into the interior channels 46 inside each corrugation 34.

The top 16 has a sloping surface 21 to aid in draining the culture medium out of the bottle 10. The bottom 12 may be flat or can have a concave cavity for receiving the neck of an adjacent bottle for closer nesting on the roller apparatus.

The interior surface of a 2.25 liter roller bottle having a height of about 10.5 inches and a width of about 5 inches containing 21 corrugations with an amplitude of 0.312 inches, a radius of 0.062 inches and a spacing of 0.403 inches was calculated to about 1725 cm2. This is about twice the surface area of the standard 2.25 liter bottle of the same exterior dimensions.

The roller bottle with two drain channels in opposed position is much stronger than a pleated bottle without the channels and has provided substantially increased yield of cells. However, the bottle exhibits some flexibility especially near the bottom. Since the drain channel area provided by the opposed channels was adequate, additional strengthening can be provided by forming narrow, flat axial beams on the outside surface of the bottle. Though these beams can function as a mini-channel, their primary purpose is to provide axial stiffening of the bottle. The number of beams or ribs can be from 2 to 10 preferably 4 to 6 evenly spaced around the perimeter of the bottle. All of the ribs need not be coextensive in length. Extra ribs can be concentrated in the area needing the most reinforcement such as near the bottom of the bottle. Usually these mini-ribs will only extend up to about 10-20% of the length of the pleated section of the bottle.

Figure 5:
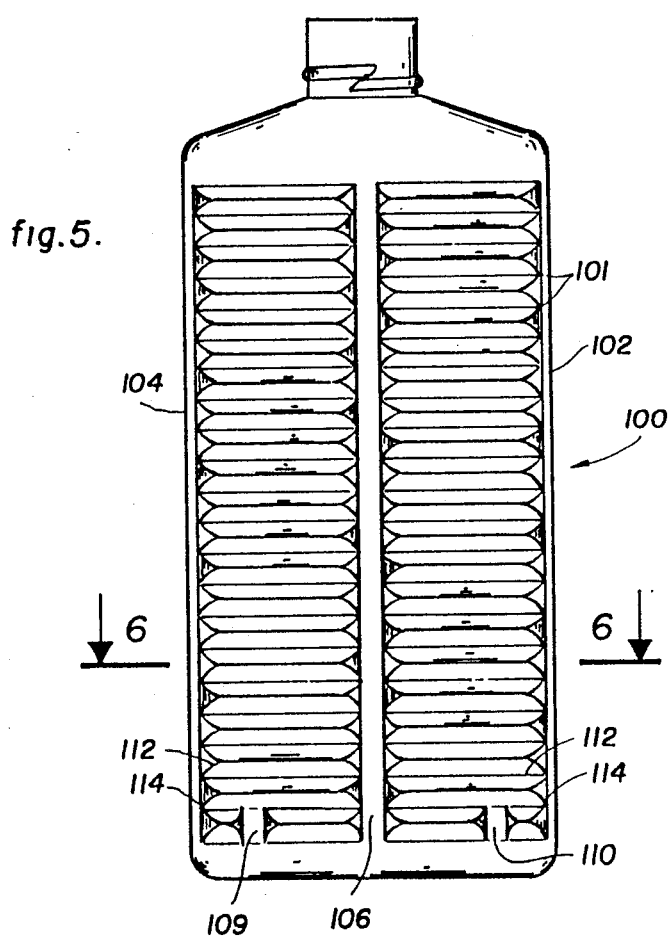
FIG. 5 is a front view in elevation of a further embodiment of a roller bottle according to the invention.
Figure 6:
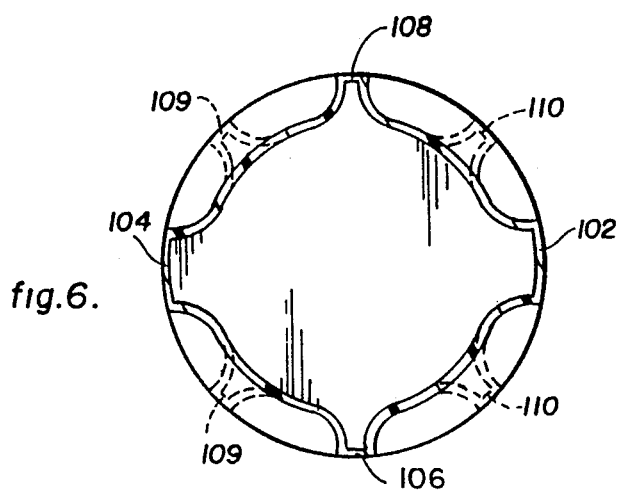
FIG. 6 is a view in-section taken along line 6—6 of FIG. 5.

Referring now to FIGS. 5 and 6, the preferred configuration of the roller bottle 100 is a bottle with corrugations 101 containing a set of opposed drain channels 102, 104; a set of opposed narrow axial ribs 106, 108 spaced 90 degrees from the center of the drain channels 102, 104 and two sets of mini-ribs 109, 110 extending up to the band 112 of the second corrugation 114. The bottle is otherwise similar to the bottle described in FIGS. 1-3.

Referring now to FIG. 4, the roller bottle 10 of the invention is first treated to prepare the surface for adhesion of cells, and is sterilized by radiation or other technique. The bottle is then filled with cells which form a layer 48 on the inside surface of the bottle. Liquid nutrient culture medium 50 is then added to the bottle and a liquid tight or breathable cap 52 is placed on the neck 18 of the bottle. The bottle is placed on horizontal rollers 54 and is rolled during processing. At an intermediate stage or at the conclusion of processing, the roller bottle is positioned with either drain channel 22, 24 in a downward position. The cap 52 is removed and the bottle 10 is tilted to drain the medium 50 from the bottle.

The roller bottles of the invention have been tested in a plurality of runs of tissue culture growth and are found to provide almost double the yield of product compared to bottles of the same exterior dimensions. The bottles are readily fabricated in one step and are found to provide good clarity and transparency even in the corrugated mid-section. The roller bottles will find use in production of vaccines and, culturing of adhering animal or human cells.

It is to be realized that only preferred embodiments of the invention have been described and that numerous substitutions, modifications and alterations are permissible without departing from the spirit and scope of the invention as defined in the following claims.

We claim:

1. A method of culturing cells comprising the steps of:
    attaching a layer of cells to the interior surface of a cylindrical synthetic resin roller bottle having a pleated segment with pleats disposed crosswise to the axis of the bottle and including at least one flat , unpleated axial panel forming at least 5% of the circumference of the plated segment for forming a drain panel for emptying the contents of the bottle, said roller bottle having a surface at least 110% the surface of a roller bottle having an unpleated cylindrical segment having the same external diameter;
    adding a culture medium to the interior surface of the roller bottle;
    rolling the bottle while culturing the cells;
    orienting the bottle with the drain panel facing downwardly; and
    tilting the bottle to drain the culture medium and cells from the bottle.

2. A method according to claim 1 in which the pleats are disposed perpendicular to the axis of the bottle.

3. A method according to claim 1 in which two opposed panels are provided in said pleated segment.

4. A method according to claim 1 in which the pleats are symmetrical.

5. A method according to claim 1 in which each panel forms at least 6.5% of the circumference of the pleated segment.

6. A method according to claim 1 in which the roller bottle is a standard roller bottle and the roller bottle contains 1-4 of said panels and the panels form 5-20% of the circumference of the pleated segment.

7. A method according to claim 1 in which the roller bottle has a surface at least 160% the surface of a roller bottle having an unpleated cylindrical segment having the same external diameter and containing 10-50 pleats.

8. A method according to claim 1 further including a top section connected to one edge of the pleated segment, said top section including a first cylindrical band absent crosswise pleats and a neck and further including a bottom section connected to the other edge of the pleated segment, said bottom section including a second cylindrical band absent crosswise pleats and a bottom wall.

9. A method according to claim 1 including from 20 to 40 pleats and having a surface area at least 200% the surface area of a roller bottle having an unpleated segment having the same external diameter.

10. A method according to claim 1 in which the interior surface is radiation treated to be wettable for attachment and growth before the layer of cells is applied.

11. A method according to claim 10 in which the interior surface is plasma treated before the layer of cells is applied.

12. A method according to claim 1 in which the bottle contains a plurality of axial support ribs narrower than the panels.

13. A method according to claim 12 in which a portion of the ribs extend across less than all of the pleats.

14. A method according to claim 1 in which each of the crosswise pleats contains an outer rim disposed in a common cylindrical plane and contains a trough on the inside surface of the pleat.

15. A method according to claim 14 in which each of said panels are connected to said troughs and are disposed no nearer to said central axis than said common cylindrical plane and the panels extend substantially across all of said pleats.

16. A method according to claim 1 in which the roller bottle is formed of a clear, sterilizable and wettable resin.

17. A method according to claim 16 in which the resin is an alkylene glycol polyester.

18. A method according to claim 17 in which the resin is a polythylene glycol terephthalate polymer.

19. A method according to claim 18 in which the resin is an ethylene glycol -1,4 cyclohexane dimethanol terephthalate copolyester.

20. A method of culturing cells comprising the steps of:

attaching a layer of cells to the interior surface of a cylindrical, synthetic resin roller bottle having a substantially cylindrical wall section containing a pleated segment containing a plurality of pleats disposed crosswise to the axis of the bottle, each of the pleats containing an outer edge disposed in a common cylindrical plane and forming a trough on the inside surface of the segment, said roller bottle having an interior surface that has been plasma treated to be wettable for cell attachment and growth and having a surface at least 160% the surface of a roller bottle having an unpleated cylindrical segment having the same exterior diameter adding a culture medium to the interior surface of the roller bottle;

rolling the bottle while culturing the cells; and tilting the bottle to drain the culture medium and cells from the bottle.

* * * * *